United States Patent [19]

Satzinger et al.

[11] 3,931,212
[45] Jan. 6, 1976

[54] METHOD FOR TREATING CARDIOVASCULAR CIRCULATORY INSUFFICIENCIES AND HYPOTONIA WITH 2-HYDROXY-PHENYL-1-OXA-4-AZASPIROALKANE DERIVATIVES

[75] Inventors: Gerhard Satzinger, Denzlingen; Manfred Herrmann, St. Peter, both of Germany

[73] Assignee: Warner-Lambert Company, Morris Plains, N.J.

[22] Filed: June 28, 1974

[21] Appl. No.: 484,376

[30] Foreign Application Priority Data
July 19, 1973 Germany.......................... 2336746

[52] U.S. Cl............................ 260/307 FA; 424/272
[51] Int. Cl.²................................. C07D 263/06
[58] Field of Search............................. 260/307 FA

[56] References Cited
UNITED STATES PATENTS
3,565,905  2/1971  Maillard.......................... 260/294.7

OTHER PUBLICATIONS

Bretschneider, C. A. 43, 2602i (1949).

Kametani et al., Chem. Pharm. Bull. 17 (11), 2353–2355 (1969).

*Primary Examiner*—Raymond V. Rush
*Attorney, Agent, or Firm*—Albert H. Graddis; Frank S. Chow; George M. Yahwak

[57] ABSTRACT

2-Hydroxy-phenyl-1-oxa-4-azaspiroalkane derivatives, the preparation thereof, and pharmaceutical compositions containing these 2-hydroxyphenyl-1-oxa-4-azaspiroalkane derivatives are disclosed. These derivatives possess unexpectedly valuable therapeutic properties which make them outstandingly useful for the treatment of cardiovascular circulatory insufficiencies and hypotonic states.

4 Claims, No Drawings

METHOD FOR TREATING CARDIOVASCULAR CIRCULATORY INSUFFICIENCIES AND HYPOTONIA WITH 2-HYDROXY-PHENYL-1-OXA-4-AZASPIROALKANE DERIVATIVES

The compounds according to the present invention are previously unknown with the exception of 2-(3'-hydroxyphenyl)-1-oxa-4-azaspiro[4,5]decane, which has been described in *Chem. Pharm. Bull.*, 17 (11), 2353-7, 1969. Nothing, however, is said concerning its use. Furthermore, no compounds with the 1-oxa-4-azaspiroalkane structure have been described which are known to have an anti-hypotensive action.

The 2-(3'-hydroxyphenyl)-1-oxa-4-azaspiroalkanes with which the present invention is concerned are compounds and the pharmaceutically acceptable salts thereof, having the general formula:

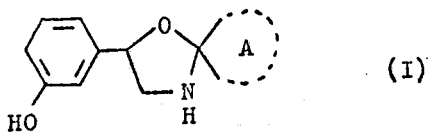

(I)

wherein A is a carbocyclic ring containing 5–8 carbon atoms which is optionally substituted by lower alkyl radicals or hydroxyl groups. The ring can also be bridged and can also contain one or two double bonds. With the exception of the compound of general formula (I) in which A is a simple carbocyclic ring containing 5 carbon atoms, these compounds are new.

The ring system A can be varied within wide limits, i.e. it can be monocyclic, bicyclic or polycyclic and can also contain one or two double bonds. Thus, a carbocyclic ring A can be derived, for example, from the following cyclic hydrocarbons: cyclopentane, methylcyclopentane, ethylcyclopentane, pentylcyclopentane, cyclohexane, isopropylcyclohexane, dimethylcyclohexane, cyclohex-1,3-diene, cycloheptane, cyclohepta-1,4-diene, dimethylcyclohepta-1,4-diene, cyclooctane, bicyclo[2,2,1]heptane, bicyclo[3,2,1]octane and bicyclo[4,2,0]octane.

Those compounds of general formula (I) are preferred in which A is a carbocyclic ring of the general formula:

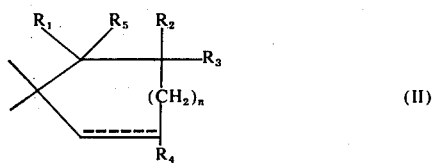

(II)

wherein $R_1$, $R_2$, $R_3$ and $R_5$, which may be the same or different, are hydrogen atoms or straight-chained or branched alkyl radicals containing up to 3 carbon atoms; $R_4$ is a hydrogen atom, a hydroxyl group, a methyl radical, or, together with $R_5$, a straight-chained or branched alkylene bridge containing up to 3 carbon atoms; $n$ is 1, 2, or 3; and the dotted line indicates the optional presence of a double bond.

In a further preferred group of compounds, in the ring A of general formula (I), $R_1$, $R_2$ and $R_3$, which may be the same or different, are hydrogen atoms or methyl radicals; $R_4$ is a hydrogen atom, a hydroxy group, or a methyl radical; $R_5$ is a hydrogen atom, or, together with $R_4$, represents an isopropylidene bridge; $n$ is 1 or 2. The dotted line represents a double bond when $R_4$ is a hydroxyl group.

An especially preferred compound is 2-(3'-hydroxyphenyl)-1-oxa-4-azaspiro[4,6]undecane, either in the form of the free base or in the form of a salt with a pharmacologically compatible acid, preferably its hydrochloride.

The compounds of general formula (I) can be prepared, for example, by reacting 1-(3'-hydroxyphenyl)-2-amino-ethanol with a ketone of the general formula:

III wherein A has the same meaning as above. The reaction can be carried out in a polar solvent or in a mixture of polar solvents, preferably at a temperature between about 20° and 140°C. If desired, the compound (I) obtained can be converted into a salt by reaction with a pharmacologically compatible inorganic or organic acid.

As polar solvents, there can be used all the conventional solvents which are inert under the reaction conditions, for example methanol, ethanol, isopropanol, dimethyl formamide, dioxan or acetonitrile. The ketone (III), when used in excess, can also act as solvent for carrying out the reaction.

The 1-(3'-hydroxyphenyl)-2-aminoethanol used as starting material is also known as norfenefrin.

The ketones of general formula (III) are either described in the literature or can be prepared following known procedures.

In carrying out the reaction, expecially high yields are obtained when the 1-(3'-hydroxyphenyl)-2-aminoethanol is used in the form of a salt, preferably as the hydrochloride, and when, as polar solvent, there is used an excess of ketone of general formula (III). The water of reaction formed can be removed azeotropically by means of an entraining agent, for example benzene or toluene, at an elevated temperature, for example 80°–140°C. Irrespective of the last-mentioned measures and due to the use of the amine in the form of a salt, not only is the yield increased but, unexpectedly, the reaction velocity is also considerably increased.

By means of the process according to the present invention, it is now possible to prepare compounds of general formula (I) in which A is a highly substituted and/or complex carbocyclic ring. Thus, the corresponding ketones of general formula (III) are, for reasons of steric hindrance, of such low reactivity that they cannot be reacted under conventional reaction conditions. It must also be pointed out that not only the free aminoethanol but also some of the ketones of general formula (III) are so labile that, especially under more drastic reaction conditions, side reactions such as autoxidation and autocondensation occur to a considerable extent. These disadvantages are substantially avoided by the process according to the present invention.

The pharmacologically compatible salts of the compounds of general formula (I) can be prepared in the usual manner, for example by neutralization of the free bases (I) with pharmacologically compatible inorganic or organic acids, such as hydrochloric, sulphuric, phosphoric, hydrobromic, acetic, lactic, citric, malic, salicylic, malonic, maleic and succinic acids.

The present invention also provides pharmaceutical compositions for the treatment of cardiovascular circulatory insufficiencies and of hypotonic states in mammals comprising at least one compound of the general formula (I) and/or at least one pharmacologically compatible salt thereof in admixture with a solid or liquid pharmaceutical diluent or carrier for enteral or parenteral administration. As injection medium, water is preferably used which contains the usual additives for injection solutions, such as stabilizing agents, solubilizing agents, and buffers. Among additives of this type are, for example, tartrate and citrate buffers, ethanol, complex-forming agents (such as ethylenediamine-tetraacetic acid and the non-toxic salts thereof), and high molecular weight polymers (such as liquid polyethylene oxide) for viscosity regulation. Solid carrier materials include, for example, starch, lactose, mannitol, methyl cellulose, talc, highly disperesed silicic acid, high molecular weight fatty acids (such as stearic acid), gelatine, agar-agar, calcium phosphate, magnesium stearate, animal and vegetable fats, and solid high molecular weight polymers (such as polyethylene glycols); compositions suitable for oral administration can, if desired, contain flavoring and/or sweetening agents.

The dosage of the compounds used depends upon the nature and severity of the circulatory disease to be treated. In the case of hypotonias, the effective oral single dose was found to be about 3–15 mg. per kg. of body weight and the effective intravenously or subcutaneously administered single dose was found to be about 0.1–2 mg. per kg.

The following experimental results demonstrate the superiority of the compounds of general formula (I) in comparison with norfenefrin and etilefrin, which represent the closest known prior art:

I. Toxicity was determined on mice in the usual manner; the test and comparison substances being administered in aqueous solution by means of a stomach probe.

II. Sympathomimetic action was determined by measurement of the arterial and venous blood pressure using Statham transducers. The measured values were recorded by means of a direct recording instrument.

As experimental animals, adult dogs of both sexes were used; these had been narcotised with pentobarbital. During the experiment, the animals were kept at their specific body temperature by means of rectum-controlled infra-red lamps.

The compounds tested were injected, in the form of an isotonic solution, into the side branch of the vena femoralis.

In the case of intraduodenal administration, the animals were laparotomised, and a cannula was fixed into the small intestine so that the substance, in the form of an aqueous solution, could be introduced directly into the intestine. Furthermore, the pylorus was ligatured in order to prevent regurgitation of the substance into the stomach.

In the case of intragastric administration, the substances were administered in the form of an aqueous solution by means of a stomach probe.

Quiet and compatible dogs were trained to lie, without sedation, for a few hours on an operating board. Under local anaesthesia, a catheter was introduced into the arteria femoralis. A measurement of arterial blood pressure was then carried out using the catheter and a Statham transducer.

The results obtained are set out hereinafter in tabular form. In these tables, the following test compounds are referred to:

A = 2-(3'-hydroxyphenyl)-1-oxa-4-azaspiro[4,5]-decane

B = 2-(3'-hydroxyphenyl)-1-oxa-4-azaspiro[4,6]undecane

C = 7,9,9-trimethyl-2-(3'-hydroxyphenyl)-1-oxa-4-azaspiro[4,5]dec-6-ene.

D = 1-(3'-hydroxyphenyl)-2-aminoethanol (norfenefrin)

E = 1-(3'-hydroxyphenyl)-2-ethylaminoethanol (etilefrin).

TABLE I

| test compound | Toxicity largest dose i.v. at which all animals survive mg/kg | $LD_{50}$ i.g. mg/kg. |
|---|---|---|
| A | 3.3 | >400 |
| B | 3.3 | ~400 |
| C | 20.7 | ~1200 |
| D | 3.3 | not determinable[+] |
| E | 7.25 | not determinable[+] |

[+]Because of insufficient resorption, there was no dosagedependent death of the animals. Thus, the results obtained cannot be statistically evaluated.

TABLE II

| test compound | Sympathomimetic action increase of the average blood pressure by 25% over the initial value (narcotised dogs) | increase of the average blood pressure in % of initial value (awake dogs) |
|---|---|---|
| A | i.d. 2.0 mg/kg >50' | i.v. 0.05 mg/kg/50–80% i.g. 4 mg/kg 40% >60' |
| B | i.g. 2.0 mg/kg >60' | i.v. 0.05 mg/kg/40–70% i.g. 2 mg/kg/35% 70' |
| C | i.g. 4.0–16.0 mg/kg 60' | i.v. 1 mg/kg/30–60% i.g. 16 mg/kg/50% 34' |
| D | i.d. >20 mg/kg | i.v. 0.05 mg/kg/50–70% i.g. up to 20 mg/kg without effect |
| E | i.d. >20 mg/kg | i.v. 0.05 mg/kg/25% i.g. up to 20 mg/kg without effect |

From the results obtained, it can be seen that these compounds possess a surprisingly high oral effectiveness in comparison with the known compounds. Thus, it is now possible to safely and effectively control hypotonia by the oral route. This is especially valuable since the oral effectiveness of the previously known sympathomimetic drugs was hitherto insufficient and uncertain.

The following Examples are given for the purpose of illustrating the present invention.

EXAMPLE 1

2-(3'-HYDROXYPHENYL)-1-OXA-4-AZASPIRO[4,5]DECANE

A suspension of 20 g. of 1-(3'-hydroxyphenyl)-2-amino-ethanol hydrochloride in 100 ml. of cyclohexanone is heated, while stirring vigorously, in a three-necked flask equipped with a dropping funnel, water separator, and thermometer. Above a temperature of 80°C., up to 100 ml. of benzene are added dropwise in such a manner so that the water of reaction formed together with the benzene is distilled of azeotropically. The temperature of the flask contents is, at the finish, about 130°C. After cooling, the crystalline reaction product is separated off, digested with benzene, and collected on a frit. There is obtained 20.3 g. (71.5% of theory) of 2-(3'-hydroxyphenyl)-1-oxa-4-azospiro[4,5]decane hydrochloride. After recrystallization from isopropanol/ethyl acetate, the product is obtained in the form of colorless crystals with a melting point of 138°–139°C.

EXAMPLE 2

2-(3'-HYDROXYPHENYL)-1-OXA-4-AZASPIRO[4,6]UNDECANE

Method A:

In a manner analogous to that described in Example 1, a suspension of 20 g. of 1-(3'-hydroxyphenyl)-2-aminoethanol hydrochloride is reacted in 100 ml. of cycloheptanone. The reaction is allowed to proceed to completion at a temperature of 120°C. After cooling, the reaction product is separated off, digested with benzene and washed with benzene on a filter funnel. There is obtained 26.4 g. (88.3% of theory) of 2-(3'-hydroxyphenyl)-1-oxa-4-azaspiro[4,6]undecane hydrochloride. After recrystallization from isopropanol, the product has a melting point of 162°–164°C.

Method B:

From 10 g. of 1-(3'-hydroxyphenyl)-2-aminoethanol hydrochloride, there is obtained a solution of the corresponding free base by the addition of sodium ethylate in anhydrous ethanol (1.2 g. of sodium dissolved in 115 ml. of absolute ethanol). After filtration, this solution is gently evaporated in a vacuum, and the residue taken up in 50 ml. of acetonitrile/ethanol (3:1), with warming. If necessary, the solution obtained is filtered. After the addition of 6.0 g. of cycloheptanone, the mixture is heated for 3.5 hours at 70°C. The product, which separates out, is isolated and recrystallized from 200 ml. of isopropanol. There is obtained 5.4 g. (44% of theory) of 2-(3'-hydroxyphenyl)-1-oxa-4-azaspiro[4,6]undecane, which has a melting point of 175°–176°.

EXAMPLE 3

7,9,9-TRIMETHYL-2-(3'-HYDROXYPHENYL)-1-OXA-4-AZASPIRO[4,5]DEC-6-ENE

Method A:

10 g. of 1-(3'-hydroxyphenyl)-2-aminoethanol hydrochloride are heated, while stirring, with 75 ml. of 1,5,5-trimethyl-cyclohex-1-en-3-one for 2 hours at 100°–110°C. The water of reaction is removed by the slow dropwise addition of about 30 ml. of benzene. The temperature can thereby be increased to a maximum of 140°C. The cooled residue is partitioned between water and ether, and the aqueous phase adjusted with ammonia to a pH of 9. Some ether is then added, and the precipitated product crystallized. There is obtained 10.6 g. (74% of theory) of 7,9,9-trimethyl-2-(3'-hydroxyphenyl)-1-oxa-4-azaspiro[4,5]dec-6-ene, which has a melting point of 171°–172°C., (after recrystallization from isopropanol).

Method B:

From 21.5 g. of 1-(3'-hydroxyphenyl)-2-aminoethanol hydrochloride there is prepared, by addition of sodium ethylate in anhydrous ethanol, a solution of 17.5 g. of 1-(3'-hydroxyphenyl)-2-aminoethanol. After filtration, the solution is gently evaporated in a vacuum and the residue taken up with acetonitrile/ethanol (3:1) solution. The solution is filtered and the filtrate is mixed with 16.8 ml. (15.5 g.) of 1,5,5-trimethylcyclohex-1-en-3-one (isophorone). The reaction mixture is heated for 5 hours at 75°C., the solvent removed in a vacuum, and the residue partitioned between water and ether. The reaction product, which separates out from the ethereal phase, is isolated and recrystallized from isopropanol. There is obtained 10.8 g. (35% of theory) of 7,9,9-trimethyl-2-(3'-hydroxyphenyl)-1-oxa-4-azaspiro[4,5]dec-6-ene, which has a melting point of 172°–173°C.

EXAMPLE 4

6-METHYL-(6,9-ENDO-DIMETHYLMETHYLENE-2-(3'-HYDROXYPHENYL)-1-OXA-4-AZASPIRO[4,5]DECANE

In a manner analogous to that described in Example 3, from 50 g. of 1-(3'-hydroxyphenyl)-2-aminoethanol hydrochloride there is prepared a solution of about 41 g. of the free base in 250 ml. acetonitrile/ethanol (3:1) solution. The solution is mixed with 38 g. of camphor dissolved in 50 ml. acetonitrile, and heated under reflux for 5 days. The reaction mixture is then worked up in the manner described in Example 3. After recrystallization from isopropanol, there is obtained 12.2 g. of 6-methyl-(6,9-endo-dimethyl-methylene)-2-(3'-hydroxyphenyl)-1-oxa-4-azaspiro[4,5]decane, which has a melting point of 185°–187°C.

EXAMPLE 5

9,9-DIMETHYL-7-HYDROXY-2-(3'-HYDROXYPHENYL)-1-OXA-4-AZAspiro[4,5]DEC-6-ENE

In a manner analogous to that described in Example 3B, from 21.5 g. of 1-(3'-hydroxyphenyl)-2-aminoethanol hydrochloride, there is prepared a solution of 17.5 g. of the base in 100 ml. acetonitrile/ethanol (3:1) solution. The solution is mixed with 14 g. of 5,5-dimethyl-cyclohexane-1,3-dione (dimedone—the dimedone reacting as a cyclohex-2-en-3-ol-1-one). After heating the reaction mixture under reflux for 20 hours, the precipitate formed is isolated and recrystallized from ethanol/acetonitrile (6:1) solution. There is obtained 12.1 g. (44% of theory) of 9,9-dimethyl-7-hydroxy-2-(3'-hydroxyphenyl)-1-oxa-4-azaspiro[4,5]-dec-6-ene in the form of colorless crystals which have a melting point of 217°C.

Thus, in the above five examples, the carbocyclic ring A has the following structural configuration:

Example 1

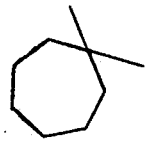

Example 2

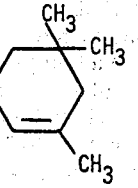

Example 3

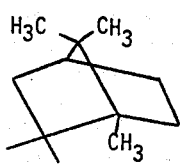

Example 4

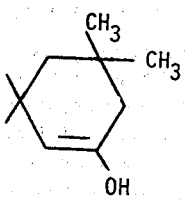

Example 5

EXAMPLE 6

FORMULATION FOR TABLETS 5 kg. of 2-(3'-hydroxyphenyl)-1-oxa-4-azaspiro[4,6]-undecane hydrochloride is completely and homogeneously mixed with a mixture of 5 kg. of polyvinyl pyrrolidone, 1 liter of ethanol, 20 kg. of lactose, 3 kg. of stearic acid, 4 kg. of talc, and 12 kg. of maize starch. This mixture is granulated and pressed into tablets with an active material content of 5 mg. per tablet.

EXAMPLE 7

5 kg. of 2-(3'-Hydroxyphenyl)-1-oxa-4-azaspiro[4,6]-undecane hydrochloride is homogeneously mixed with 30 kg. of lactose, and filled into hard gelatine capsules. The active material content of each capsule is 5 mg.

We claim:

1. The compound 2-(3'-Hydroxyphenyl)-1-Oxa-4-Azaspiro [4,6] Undecane.
2. The compound 7,9,9-Trimethyl-2-(3'-Hydroxyphenyl)-1-Oxa-4-Azaspiro[4,5]Dec-6-Ene.
3. The compound 6-Methyl-6,9-Endo-Dimethylmethylene)-2-(3'-Hydroxyphenyl)-1-Oxa-4-Azaspiro[4,5]Decane.
4. The compound 9,9-Dimethyl-7-Hydroxy-2-(3'-Hydroxyphenyl)-1-Oxa-4-Azaspiro[4,5]Dec-6-Ene.

* * * * *